US007128717B1

(12) United States Patent
Thach et al.

(10) Patent No.: US 7,128,717 B1
(45) Date of Patent: Oct. 31, 2006

(54) METHOD FOR DETERMINING AIRWAY OBSTRUCTION

(75) Inventors: Bradley T. Thach, Kirkwood, MO (US); Mary Pylipow, Eden Prairie, MN (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 11/238,271

(22) Filed: Sep. 29, 2005

(51) Int. Cl.
*A61B 5/08* (2006.01)
*A61B 5/05* (2006.01)
(52) U.S. Cl. ............... 600/533; 600/538; 600/547
(58) Field of Classification Search .............. None
See application file for complete search history.

(56) References Cited

U.S. PATENT DOCUMENTS

| 5,540,732 A * | 7/1996 | Testerman ............... 607/42 |
| 2003/0191503 A1* | 10/2003 | Zhu et al. ............... 607/17 |
| 2005/0192508 A1* | 9/2005 | Lange et al. ............ 600/534 |

OTHER PUBLICATIONS

Bass et al., "The Effect of the Chronic or Intermittent Hypoxia on Cognition in Childhood: A Review of the Evidence," Pediatrics, 2004, pp. 805-816, vol. 114.
Bolton, "The Prevalence of Immature Respiratory Control in a Neonatal Population," NZ Med. J., 1990, pp. 89-92, vol. 103.
Brouillette et al., "Comparison of Respiratory Inductive Plethysmography and Thoracic Impedance for Apnea Monitoring," J. Peds., 1987, pp. 377-383.
Brouillette et al., "Obstructive Sleep Apnea in Infants and Children," J. Peds., 1982, pp. 31-40, vol. 100.
Cheung et al., "Early Childhood neurodevelopment in Very Low Birth Weight with Predischarge Apnea," Ped. Pulm., 1999, pp. 2714-2720.
Ramanathan et al., "Cardiorespiratory Events Recorded on Home Monitors Comparison of Healthy Infants with Those at Risk for SIDS," JAMA, 2001, pp. 2199-2207, vol. 285.
Roberts et al., "Assesment of pharyngeal Airway Stability in Normal and Micrognathic Infants," Am. Physiol. Soc., 1985, pp. 290-299.
Stark et al., "Mechanisms of Airway Obstruction Leading to Apnea in Newborn Infants," J. Peds. 1976, pp. 982-985, vol. 89.
Weese-Mayer et al., "Comparison of Apnea identified by Respiratory Inductance Plethysmography with that Detected by End-Tidal CO2 or Thermister," Am. J. Respir. Crit. Care Med., 2000, pp. 471-480, vol. 162.

* cited by examiner

Primary Examiner—Robert L. Nasser
(74) Attorney, Agent, or Firm—Sonnenschein Nath & Rosenthal LLP

(57) ABSTRACT

A method of determining whether an individual's breathing is obstructed. The method includes measuring a transthoracic impedance of the individual over a predetermined time interval, identifying a baseline impedance and selecting an impedance cycle. The method also includes identifying a maximum impedance during the selected impedance cycle, determining an upper difference between the maximum impedance and the baseline impedance, identifying a minimum impedance during the selected impedance cycle, and determining a lower difference between the minimum impedance and the baseline impedance. The method includes determining whether an amplitude of the upper difference is less than about seventy percent of an amplitude of the lower difference, and notifying an observer that the amplitude of the upper difference is less than about seventy percent of the amplitude of the lower difference.

10 Claims, 2 Drawing Sheets

METHOD FOR DETERMINING AIRWAY OBSTRUCTION

BACKGROUND OF THE INVENTION

The present invention relates generally to transthoracic impedance and more particularly to a method for determining airway obstruction using transthoracic impedance.

Studies of Sudden Infant Death Syndrome (SIDS) tracings indicate three phases in the death of infants—hypoxic hyperpnea, apnea and gasping. Hypoxic hyperpnea is an abnormal increase in the depth and frequency of breaths resulting in a drop in oxygen content of air in the lungs. Apnea is a temporary cessation of breathing, and gasping is a uniquely regulated type of breathing that occurs under conditions of severe brain hypoxia. Autoresuscitation, which is defined as an increase in heart rate following a gasp, occurs less often in SIDS infants than infants dying due to other causes. Because successful lung inflation during gasping is the primary mechanism for autoresuscitation, an obstructed airway can prevent autoresuscitation potentially resulting in death.

There are two critical periods in the sudden death of infants. A first period includes factors precipitating hypoxia (i.e., a drop in oxygen content of tissue in the lungs) and a second period is a failure of gasping to alleviate hypoxia. Many SIDS infants have obstructed airways contributing to the initial hypoxia, as well as to the failure of autoresuscitation during hypoxic gasping.

Transthoracic impedance, which is a measure of the electrical impedance across an individual's thorax (i.e., the cavity in which the lungs and heart are positioned), is commonly used to monitor respiration (i.e., breathing). Because air is a relatively poor conductor of electrical current and blood is a relatively good conductor of electrical current, transthoracic impedance is an indication of the ratio of air to blood in the thorax. As the amount of air in the thorax increases, transthoracic impedance increases. Conversely, as the amount of blood in the thorax increases, transthoracic impedance decreases. Even though transthoracic impedance is an indication of the ratio of air to blood, it is not a direct measure of breathing because transthoracic impedance continues to oscillate even when the airway is obstructed. For this reason, in the past it was believed that transthoracic impedance could not be used to detect obstructive apnea because the impedance signal continues during airway obstruction.

Other methods have been explored for determining when a breath is obstructed. For example, a reduction in the sum channel of respiratory inductance plethysmography has been used to identify obstructed breaths. However, this method only detects about 54% of obstructions when compared to end tidal carbon dioxide measurements. Thus, this method is not an effective way of indicating airway obstruction. Because most infant apneas consist of obstructed breaths occurring during periods of absent respiratory efforts, the total duration of an apneic event is not documented by current methods and the monitor may not alarm in time for a caretaker to use cardio pulmonary resuscitation. Furthermore, healthcare professionals may be aware an infant is having prolonged apneic events and discontinue monitoring. Accordingly, a need exits for an effective indicator of airway obstruction to reduce occurrences of death from prolonged apneic events.

SUMMARY OF THE INVENTION

Briefly, the present invention includes a method of determining whether an individual's breathing is obstructed. The method comprises measuring a transthoracic impedance of the individual over a predetermined time interval, identifying a baseline impedance, and selecting an impedance cycle. The method further comprises identifying a maximum impedance during the selected impedance cycle, and determining an upper difference between the maximum impedance and the baseline impedance. Further, the method comprises identifying a minimum impedance during the selected impedance cycle, and determining a lower difference between the minimum impedance and the baseline impedance. In addition, the method comprises determining whether an amplitude of the upper difference is less than about seventy percent of an amplitude of the lower difference, and notifying an observer that the amplitude of the upper difference is less than about seventy percent of the amplitude of the lower difference.

In another aspect, the invention includes a method of determining whether an individual's breathing is obstructed comprising measuring a transthoracic impedance of the individual over a predetermined time interval, and identifying a baseline impedance. In addition, the method comprises determining whether an amplitude of a maximum impedance above the baseline impedance during an impedance cycle is less than a predetermined percentage of an amplitude of a minimum impedance below the baseline impedance during the impedance cycle.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
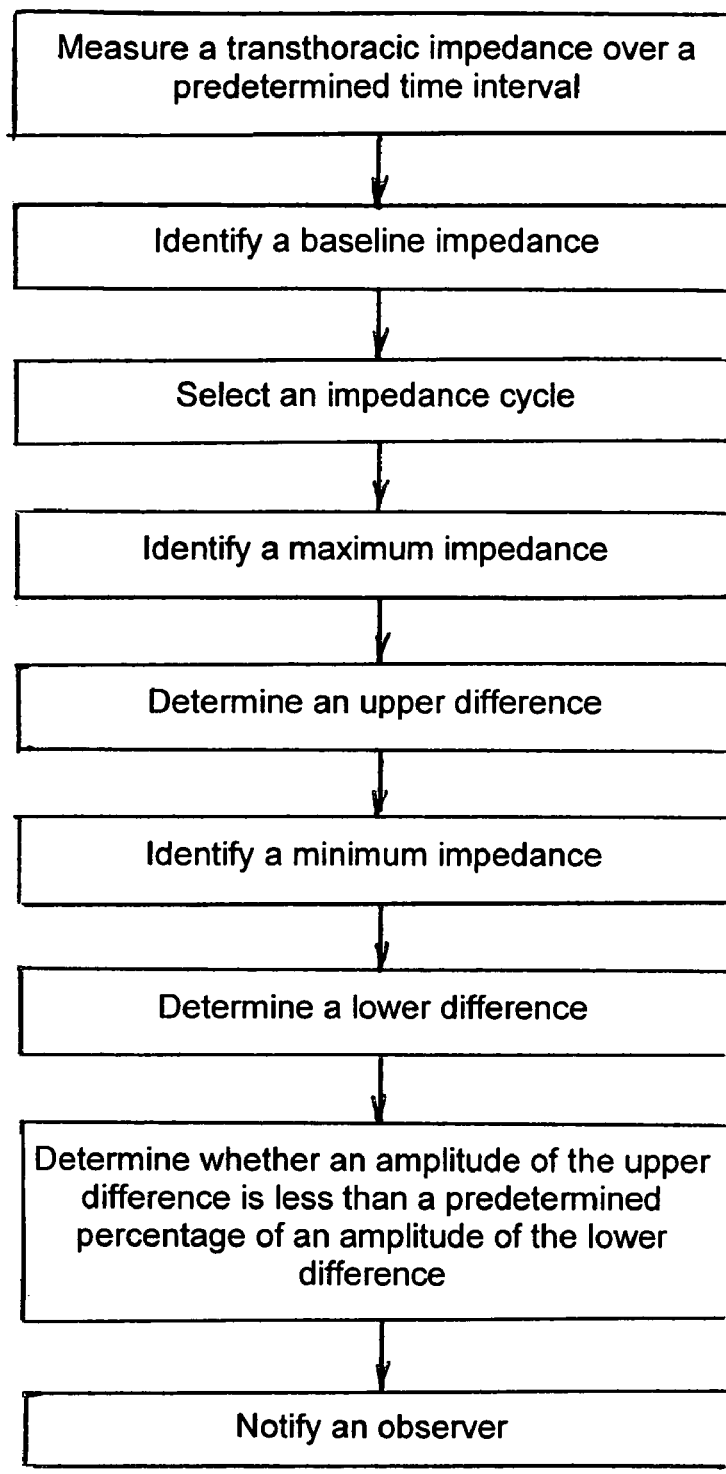
FIG. 1 is a schematic diagram illustrating a method of the present invention.

Referring now to the drawings and in particular to FIG. 1, a method of the present invention is designated in its entirety by the reference numeral 20. The method is performed using a transthoracic impedance monitor such as a Model 9500 transthoracic impedance monitor available from Aequitron Medical, Inc. of Plymouth, Minn. Other types and models of transthoracic impedance monitors may be used without departing from the scope of the present invention.

The transthoracic impedance monitor is connected to an individual and operated in a conventional manner as described in operating instructions provided by the manufacturer of the monitor. Because conventional operational details are well known by those of ordinary skill in the art, they will not be described in further detail. The transthoracic impedance monitor provides a transthoracic impedance trace as will be described in further detail below.

Figure 2:
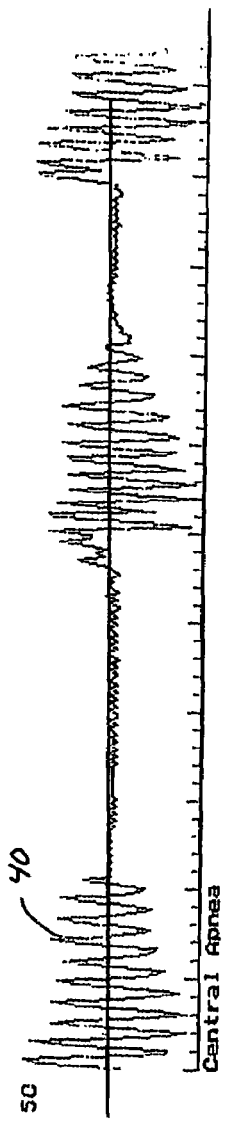
FIG. 2 is a transthoracic impedance trace for an individual without airway obstruction.

In one embodiment, the method 20 of determining whether an individual's breathing is obstructed includes measuring (step 22) a transthoracic impedance of the individual over a predetermined time interval (e.g., time interval Δt in FIG. 2.) This step is performed using a monitor such as the monitor identified above. As used herein, "individual" includes any animal, particularly an infant human and more particularly an infant human at risk for SIDS. Although the transthoracic impedance may be measured over other periods of time without departing from the scope of the present invention, in one embodiment the impedance is measured over a period during which the individual is expected to sleep (e.g., about 8 hours, about 12 hours, about 14 hours or about 16 hours from the time the individual lays down to sleep.) The method 20 continues by identifying (step 24) a baseline impedance (e.g., impedance $I_0$ in FIG. 2) by averaging a maximum and minimum impedance of a respiratory cycle. Next, an impedance cycle is selected (step 26) for evaluation (e.g., cycle $C_i$ in FIG. 2.) Although this step may be performed in other ways without departing from the scope of the present invention, in one embodiment the cycle is selected at regular intervals during the period of time over which impedance is measured. For example, a cycle may be evaluated every twenty seconds. Alternatively, every cycle may be evaluated. In another alternative, the cycles are counted and after a predetermined number of cycles have occurred since the last observation, a cycle is selected. For example, every tenth cycle may be selected. Once a cycle is selected for evaluation, a maximum impedance is identified (step 28) during the selected impedance cycle (e.g., maximum impedance $I_{maxi}$ in FIG. 2.) The method 20 continues by determining (step 30) an upper difference between the maximum impedance and the baseline impedance (i.e., $I_{maxi}-I_0$), identifying (step 32) a minimum impedance during the selected impedance cycle (e.g., minimum impedance $I_{mini}$ in FIG. 2), and determining (step 34) a lower difference between the minimum impedance and the baseline impedance (i.e., $I_{mini}-I_0$). As will be appreciated by those skilled in the art, the order of steps 28–34 may be changed. For example, step 34 may be performed before step 28 and steps 30 and 34 may follow. Next, a determination (step 36) is made whether an amplitude of the upper difference is less than a predetermined percent of an amplitude of the lower difference, and an observer is notified (step 38) that the amplitude of the upper difference is less than the predetermined percent of the amplitude of the lower difference, indicating a possibility of an obstructed airway. As will be apparent to those skilled in the art, the observer may be remote from the individual being monitored.

Although other predetermined percentages may be used for determining whether the amplitude of the upper difference is less than the predetermined percent of the amplitude of the lower difference and notifying the observer, in one embodiment the predetermined percentage is less than about seventy percent. In another embodiment, the predetermined percent is less than about fifty percent. In still another embodiment, the predetermined percent is less than about twenty five percent, and in yet another embodiment the predetermined percent is less than about ten percent. As will be appreciated by those skilled in the art, lower percentages decrease the likelihood of false alarms but increase the likelihood an obstructed airway event occurs without the observer being notified.

As will be appreciated by those skilled in the art, the methods described above may be automated and computerized. Because the algorithms and programming steps for performing these methods are well understood by those skilled in the art, they will not be described in further detail. Such automated and computerized methods are envisioned to be within the scope of the present invention.

Figure 3:
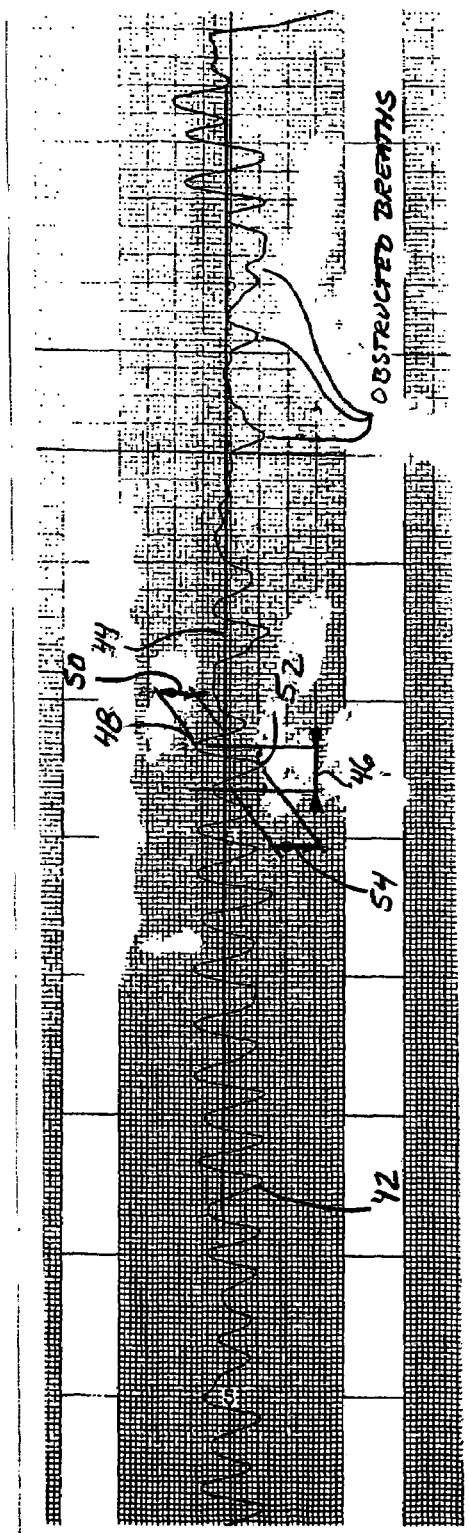
FIG. 3 is a transthoracic impedance trace for an individual with airway obstruction.

FIG. 2 illustrates a transthoracic impedance trace 40 for an individual without airway obstruction, and FIG. 3 illustrates a transthoracic impedance trace 42 for an individual with airway obstruction. The trace 42 shown in FIG. 3 is a portion of a predetermined time interval. A baseline impedance 44 ($I_0$) is identified and a particular impedance cycle 46 ($C_i$) is selected for evaluation. The maximum impedance 48 ($I_{maxi}$) is identified, and the upper difference 50 between the maximum impedance and the baseline impedance 44 ($I_{maxi}-I_0$) is determined. In addition, the minimum impedance 52 ($I_{mini}$) is identified, and the lower difference 54 ($I_{mini}-I_0$) is identified.

Verification of Efficacy of Method:

Four premature babies with apnea of prematurity and one micrognathic infant with obstructive apnea were studied for one to one and one-half hours each. Oxygen saturation, EKG, transthoracic impedance, respiratory inductance plethysmography and flow measured to binasal pneumotachography were recorded. Infants were continuously observed for activity and mouth closure. Following documentation of apnea events during sleep, experimental airway occlusions were performed. Breaths were identified as obstructed when respiratory efforts in the chest and/or abdominal respiratory inductance plethysmography tracings occurred in the absence of airflow. Obstructed breaths in the respiratory inductance plethysmography tracings were scored if the respiratory wave form in the sum channel was either absent or greatly diminished. To identify obstructed breaths in the transthoracic impedance tracing, a baseline was first established during brief periods of central apnea. Breaths were scored as obstructed when a respiratory way form larger than the cardiac artifact was negative.

A total of 201 obstructed breaths were documented during sleep with a mean of 39 breaths per infant. Of this total, 121 occurred spontaneously and 80 occurred due to experimental airway occlusions. Excluding apneas with tracings obscured by gross movement artifacts, a clear transthoracic impedance baseline could be established in 97% of the cases. The respiratory inductance plethysmography method identified 96 of the 201 obstructed breaths. The transthoracic impedance method identified 93% of the obstructed breaths. Accordingly, it is believed that a characteristic wave form in transthoracic impedance can be used to diagnose obstructed breaths.

During obstructed respiratory efforts, air flow ceases but negative thoracic pressure causes a surge in venous return. Therefore, a decrease in transthoracic impedance is expected during each obstructed breath.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method of determining whether an individual's breathing is obstructed, said method comprising:
measuring a transthoracic impedance of the individual over a predetermined time interval;
identifying a baseline impedance;

selecting an impedance cycle;

identifying a maximum impedance during the selected impedance cycle;

determining an upper difference between the maximum impedance and the baseline impedance;

identifying a minimum impedance during the selected impedance cycle;

determining a lower difference between the minimum impedance and the baseline impedance;

determining whether an amplitude of the upper difference is less than about seventy percent of an amplitude of the lower difference; and notifying an observer that the amplitude of the upper difference is less than about seventy percent of the amplitude of the lower difference.

2. A method as set forth in claim 1 further comprising:

determining whether an amplitude of the upper difference is less than about fifty percent of an amplitude of the lower difference; and notifying an observer that the amplitude of the upper difference is less than about fifty percent of the amplitude of the lower difference.

3. A method as set forth in claim 2 further comprising:

determining whether an amplitude of the upper difference is less than about twenty five percent of an amplitude of the lower difference; and notifying an observer that the amplitude of the upper difference is less than about twenty five percent of the amplitude of the lower difference.

4. A method as set forth in claim 3 further comprising:

determining whether an amplitude of the upper difference is less than about ten percent of an amplitude of the lower difference; and notifying an observer that the amplitude of the upper difference is less than about ten percent of the amplitude of the lower difference.

5. A method of determining whether an individual's breathing is obstructed, said method comprising:

measuring a transthoracic impedance of the individual over a predetermined time interval;

identifying a baseline impedance; and determining whether an amplitude of a maximum impedance above the baseline impedance during an impedance cycle is less than a predetermined percentage of an amplitude of a minimum impedance below the baseline impedance during the impedance cycle.

6. A method as set forth in claim 5 further comprising notifying an observer that the amplitude of the maximum impedance above the baseline impedance during the impedance cycle is less than the predetermined percentage of the amplitude of a minimum impedance below the baseline impedance during the impedance cycle.

7. A method as set forth in claim 6 wherein the predetermined percentage is less than about seventy percent.

8. A method as set forth in claim 7 wherein the predetermined percentage is less than about fifty percent.

9. A method as set forth in claim 8 wherein the predetermined percentage is less than about twenty five percent.

10. A method as set forth in claim 9 wherein the predetermined percentage is less than about ten percent.

* * * * *